(12) United States Patent
Guthrie et al.

(10) Patent No.: US 7,252,803 B2
(45) Date of Patent: Aug. 7, 2007

(54) HEATING OF MICROTITRE WELL PLATES IN CENTRIFUGAL EVAPORATORS

(75) Inventors: Duncan Guthrie, Nr Sudbury (GB); John Poole, Kesgrave (GB); Mike Sherwen, Woodbridge (GB)

(73) Assignee: Genevac Limited, Suffolk (GB)

( * ) Notice: Subject to any disclaimer, the term of this patent is extended or adjusted under 35 U.S.C. 154(b) by 530 days.

(21) Appl. No.: 10/276,964

(22) PCT Filed: Apr. 24, 2002

(86) PCT No.: PCT/GB02/01939

§ 371 (c)(1),
(2), (4) Date: Aug. 8, 2003

(87) PCT Pub. No.: WO02/087766

PCT Pub. Date: Nov. 7, 2002

(65) Prior Publication Data

US 2004/0200580 A1 Oct. 14, 2004

(30) Foreign Application Priority Data

Apr. 28, 2001 (GB) .................................. 0110449.6

(51) Int. Cl.
*B01L 9/06* (2006.01)
*B65D 1/34* (2006.01)
*B01D 1/14* (2006.01)
(52) U.S. Cl. .................. 422/104; 422/99; 422/100; 422/102; 159/6.1; 206/562; 206/563; 206/564; 211/71.01; 211/126.1
(58) Field of Classification Search .......... 422/99–100, 422/72, 64, 67, 101, 82.05, 82.12, 82.13, 422/62, 102, 104; 159/6.1, 44, 47.1; 436/45, 436/180; 206/562–564; 211/74, 79
See application file for complete search history.

(56) References Cited

U.S. PATENT DOCUMENTS 3,940,249 A * 2/1976 McClurg .................... 436/174

(Continued)

FOREIGN PATENT DOCUMENTS

| DE | 3941168 A1 | 6/1990 |
| GB | 2334688 A | 9/1999 |
| WO | WO 01/04600 A1 | 1/2001 |

*Primary Examiner*—Brian R. Gordon
(74) *Attorney, Agent, or Firm*—Wood, Herron & Evans, LLP (57) ABSTRACT

A method of protectively heating a microtitre well plate from below using infra-red radiation in a centrifugal evaporator, wherein a barrier plate is placed in contact with and surrounding the lower ends of the wells. The barrier plate is adapted to convey heat energy to the wells and contents thereof and is selected to be substantially non-transmittive of radiation having wavelengths in the range 200 nm to 3000 nm, and the surface of the barrier plate which is to receive the wells includes a plurality of sockets in which the closed lower ends of the wells are a snug fit. The plate is adapted to fit between the underside of the wells and a swinging sample holder mount of a centrifugal evaporator, or a shelf of a swinging sample holder mount, having two or more shelves for stacking well plates one above the other in such an evaporator. The plate is adapted to fit wholly within the envelope of the external wall of the well plate, and is dimensioned so that a gap exists between the external edge of the barrier plate and the interior of the external wall of the well plate and protrusions along some or all of the edges of the barrier plate engage the interior of the said external wall and frictionally hold the barrier plate in place.

6 Claims, 9 Drawing Sheets

U.S. PATENT DOCUMENTS

| | | | | |
|---|---|---|---|---|
| 4,124,122 A * | 11/1978 | Emmitt | | 211/74 |
| 4,389,374 A * | 6/1983 | Sutton et al. | | 422/104 |
| 4,407,958 A * | 10/1983 | DeGraff, Jr. | | 435/283.1 |
| 4,956,150 A * | 9/1990 | Henry | | 422/102 |
| 4,963,493 A * | 10/1990 | Daftsios | | 422/104 |
| 5,148,919 A * | 9/1992 | Rubin | | 206/443 |
| 5,427,743 A * | 6/1995 | Markin | | 422/104 |
| 5,670,120 A * | 9/1997 | Degenhardt et al. | | 422/104 |
| 5,710,381 A * | 1/1998 | Atwood et al. | | 73/864.91 |
| 5,948,365 A * | 9/1999 | Macy et al. | | 422/102 |
| 6,106,784 A * | 8/2000 | Lund et al. | | 422/104 |
| 6,309,608 B1 * | 10/2001 | Zhou et al. | | 422/131 |
| 6,337,435 B1 * | 1/2002 | Chu et al. | | 136/242 |
| 6,358,470 B1 * | 3/2002 | Higuchi | | 422/63 |
| 6,368,561 B1 * | 4/2002 | Rutishauser et al. | | 422/99 |
| 6,558,947 B1 * | 5/2003 | Lund et al. | | 435/303.1 |
| 6,572,828 B1 * | 6/2003 | Potyrailo et al. | | 422/130 |
| 6,605,474 B1 * | 8/2003 | Cole | | 436/177 |
| 6,640,891 B1 * | 11/2003 | Oldenburg | | 165/253 |
| 6,824,738 B1 * | 11/2004 | Neeper et al. | | 422/72 |
| 2002/0108917 A1 * | 8/2002 | Maruyama | | 211/74 |

* cited by examiner

SECTION X-X

HEATING OF MICROTITRE WELL PLATES IN CENTRIFUGAL EVAPORATORS

The present application is a filing under 35 U.S.C. 371 of PCT/GB02/01939, filed Apr. 24, 2002, which is a PCT filing of United Kingdom 0110449.6, filed Apr. 28, 2001.

FIELD OF INVENTION

This invention concerns centrifugal evaporators and processes for evaporation primarily for separating volatile components from less volatile components of liquid mixtures, typically volatile solvents in liquid mixtures.

BACKGROUND TO THE INVENTION

In the preparation of pharmaceuticals and drugs it is a common requirement to separate unwanted volatile solvent components from less volatile materials and one technique which has been developed involves centrifuging the mixture whilst simultaneously evacuating the chamber containing the centrifuged material so as to draw off from the mixture the more volatile component and leave the less volatile material behind. Thus chemists and biologists frequently need to remove liquids in which the solid matter in which they are interested is dissolved or suspended. The solid matter may be potential new drugs, biological samples or other materials. They are frequently sensitive to heat, so that the mixture cannot be boiled off at atmospheric pressure because this would involve excessively high temperatures. Boiling, or evaporation under vacuum is often the preferred process because this can be done at low temperatures which do not harm the samples. If samples in liquids are exposed to vacuum they tend to boil vigorously and this activity can lead to liquid containing valuable sample material being spilled or lost, or worse, to cross-contamination of samples which may have been expensively purified.

It is therefore well known to spin such samples in a closed vacuum chamber so as to subject them to rotation generated centrifugal forces which suppress the spitting or frothing of the liquid while it is boiling under vacuum. This process is known as Centrifugal Evaporation, or Concentration.

If such a Centrifugal Evaporator is to achieve rapid evaporation of solvents it is necessary to heat the samples to provide the energy necessary to sustain evaporation. One well known method of heating is by the use of infra red radiation from lamps located in the wall of the vacuum chamber. Once the solvent within the receptacle is boiling, the rate of evaporation is governed only by the rate of heat input to the solvent.

One known method of operation is to locate the receptacle in which the sample is contained in a holder that will allow infra red radiation from the lamps to heat the solvent in the receptacle directly. This method has the disadvantage that when the solvent in the receptacle is all evaporated, the temperature of the remaining solid compounds cannot be controlled and will increase very rapidly unless the infra red lamps are turned off. Many of the biological compounds that are regularly dried by these evaporators are highly temperature sensitive. A further disadvantage is that the solids while in solution and when dry are subjected to possibly damaging levels of radiation in wavelengths from ultra violet through visible to infra red. With the development of genetic testing using Oligonucleotide Probes it is becoming increasingly common for such probes to contain a "marker", and these markers are often sensitive to radiation and can therefore be damaged by a broad range of wavelengths including the range from ultra violet through visible to infra red.

An alternative known method aimed at overcoming the problem of temperature control highlighted above is to locate the receptacle in one or more solid aluminium blocks. In this case the block will protect the dried compounds from direct infra red radiation. The radiation from the lamps will heat the block and in turn heat will be transferred to the solvent by conduction between the sample receptacle and the aluminium block. This method gives good temperature control of the samples but has the disadvantage of slow evaporation with some formats of sample receptacle. Receptacles such as Microtitre plates give particularly slow evaporation when conduction is used to transfer the heat required for evaporation into the plate.

An alternative approach is to use a filter positioned between the IR source and the aperture into the chamber. Such filters are practical in filtering out harmful radiation in the range of wavelengths from 200 nm meters through to 600 nm but above this figure such filters start to significantly reduce the energy transfer from the source into the evaporation chamber.

It is an object of the present invention to provide means to allow use of infra red lamps to speed the evaporation of the solvent when the samples are contained within microtitre plates, or other similar formats.

SUMMARY OF THE INVENTION

According to one aspect of the invention where a microtitre well plate is to be heated from below using infra-red radiation, barrier means is placed in contact with the lower ends of the wells for conveying heat energy to the wells and contents thereof, but serving to block radiation in the wavelengths 200 nm to 3000 nm.

Typically the surface of the barrier means which is to engage the underside of the wells in the microtitre well plate is shaped so as to define a plurality of sockets in which the closed lower ends of the wells are a snug fit, whereby heat is efficiently conducted through the thermally conductive material of the barrier means to the bottom, and the wall near the lower end, of each well, to heat the contents of the well.

The barrier means may comprise a plate of thermally conductive material (but which does not transmit radiation in the range 200 nm to 3000 nm) which is of generally uniform thickness but includes a plurality of well receiving sockets in its upper surface which is to engage the underside of the microtitre well plate.

A key feature of such a shaped plate of thermally conductive material is that it presents a uniform heat transmission path to all the wells of the microtitre well plate, ensuring even evaporation of the contents of the wells.

A barrier plate as aforesaid can be designed to fit between a microtitre well plate and a swinging sample holder mount of known centrifugal evaporators, or alternatively can be designed to fit between a microtitre well plate and either shelf of a swinging sample holder mount, having two or more shelves for stacking microtitre well plates one above the other.

Preferably the barrier plate fits wholly within the envelope of the external wall of the microtitre well plate.

Preferably the barrier plate is dimensioned so that a gap exists between the external periphery and the interior of the external wall of the microtitre well plate and protrusions along some or all of the edges of the barrier plate engage the interior of the said external wall and frictionally hold the barrier plate in place.

The barrier plate should not protrude below the base of the microtitre well plate external wall, so that the overall height of the microtitre well plate is not increased.

In testing of microtitre well plates fitted with such barrier plates, it has been found possible to achieve twice the heat flow into the samples as compared with traditional methods. In most cases, this improvement will approximately halve the time required for evaporation. For example a 96 well plate with 1 ml of aqueous solution per well can take 9.5 hours to evaporate using traditional methods. By employing a barrier means in accordance with the invention, this time has been reduced to less than 5 hours.

The invention thus provides a barrier plate adapted to receive and make good internal contact with the lower ends of the wells, ensure uniform sample temperature over the well plate and protect the samples from harmful effects of radiation having wavelengths in the range 200 nm to 3000 nm. The barrier plate may engage the sample holder, which may be a so-called swinging sample holder, in which the microtitre well plate is mounted.

The invention also lies in a centrifugal evaporator which comprises an enclosure, a rotatable table therein, swinging sample holder support means carried by the table for retaining microtitre well plates therein, which during centrifuging swing through approximately 90° so that the wells are generally horizontal, and the lower ends of the wells can be heated by IR radiation, centrifugal forces acting on the liquid in the wells assisting in preventing loss of sample material other than by evaporation, and infra red radiation heating means for heating the lower ends of the wells characterised by a thermally conductive barrier plate means shielding the lower ends of the wells from direct radiation from the heating means, which plate means intimately surrounds at least the lower end of each well to provide good thermal transfer from the plate means to the wells, and the plate material is selected to protect the sample material from radiation having wavelengths in the range 200-3000 nm.

DETAILED DESCRIPTION OF THE PREFERRED EMBODIMENT

Figure 1:
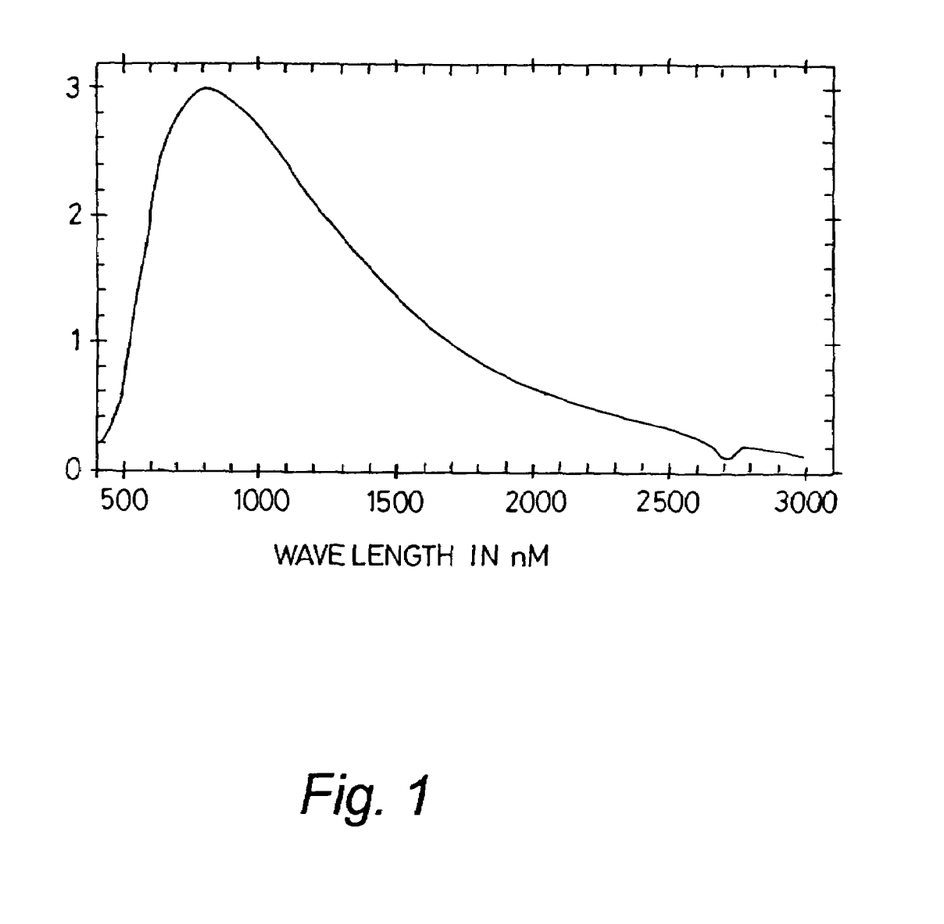
FIG. 1 shows the emission versus wavelength characteristics of a typical heating lamp used within a centrifugal evaporator.
Figure 2:
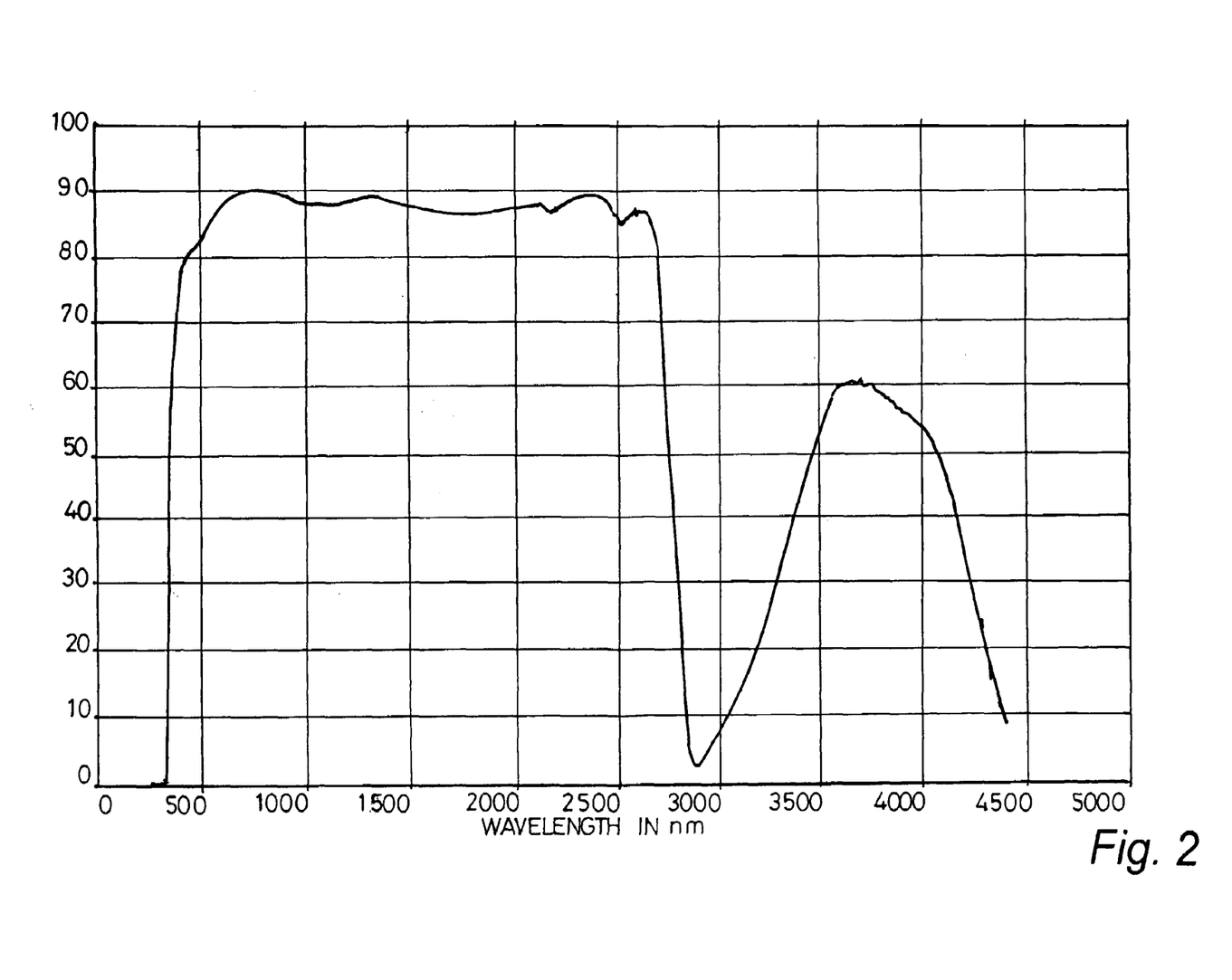
FIG. 2 shows the transmission characteristics of typical filters used between a lamp and samples in a centrifugal evaporator.

FIG. 1 shows how the emissions from a halogen-infrared reflector lamp type HLX 64635 (15v/150 w) varies with wavelength in the range 500-3000 nm, and FIG. 2 illustrates the percentage transmission efficiency of a Robax (registered trademark) 3 mm lens-filter over wavelengths in the range 0-5000 nm. It will be seen that there is a sharp fall-off in transmissivity below wavelengths of 500 nm and above wavelengths of 3000 nm. Such filters are employed in centrifugal evaporators between a lamp having an emission spectrum similar to that of FIG. 1, and a sample or samples.

Figure 3:
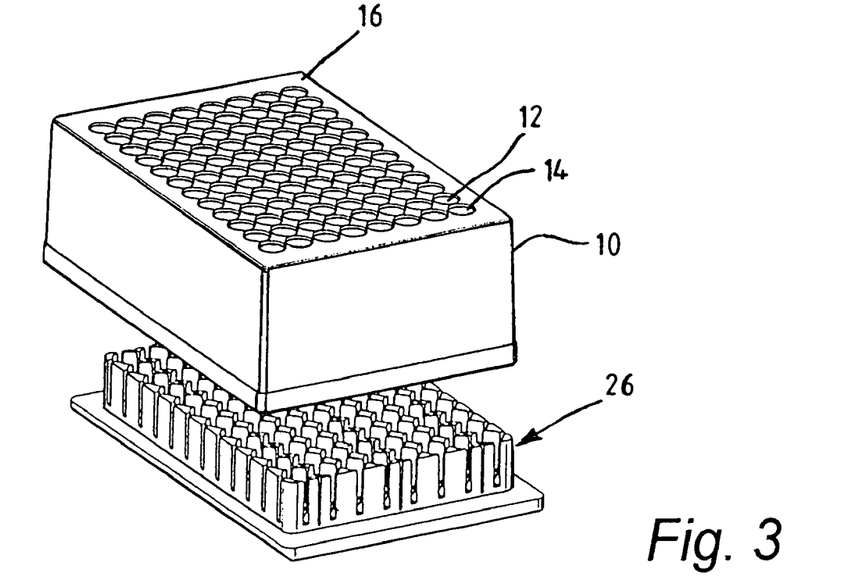
FIG. 3 shows a typical microtitre well plate and a shaped barrier means for maximizing the heat transfer into the microtitre plate, constructed as an embodiment of the present invention.
Figure 4:
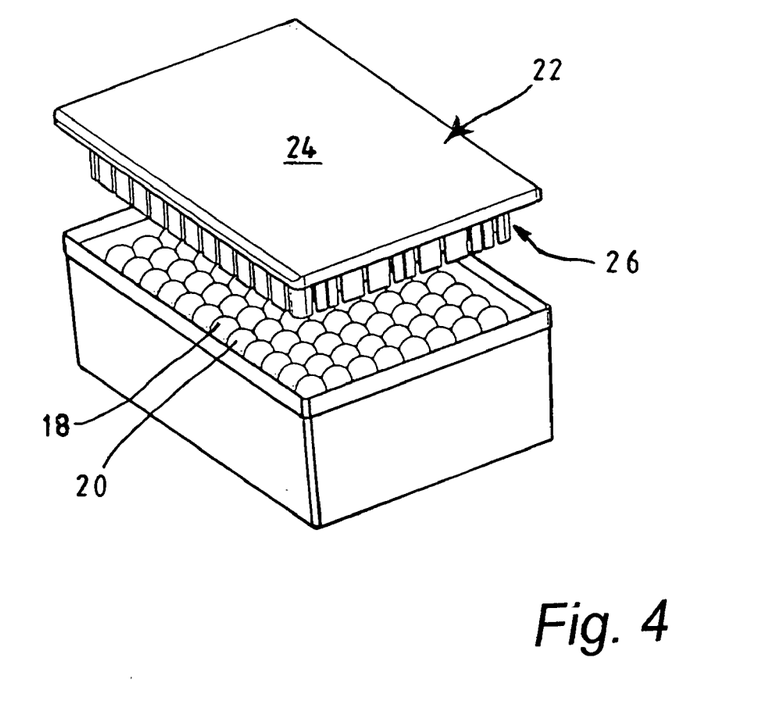
FIG. 4 is a similar perspective view of the two components making up FIG. 3, but this time with the barrier means above the microtitre plate, both components having been inverted.

A conventional microtitre moulded well plate housing 10 is shown in the perspective view of FIG. 3. The wells form a closely spaced regular matrix of openings such as 12, 14 in the upper surface 16 of the moulding. In FIG. 4, the same well plate is shown in reverse, revealing the hemispherical lower ends of the wells, such as 18, 20.

In accordance with the invention, a heat transfer plate radiation barrier 22 is provided, formed, typically, by casting, machining from solid or moulding, from a material having good thermal conductivity. The underside 24 of the plate 22 is flat, as shown in FIG. 4, while the other face includes a central raised platform 26 which is adapted to fit into the open lower end of the well plate housing. The platform is discontinuous so as to form a plurality of hemispherical concave cavities on the same matrix spacing as the rows and columns of hemispherical convex well-ends such as 18, 20 (FIG. 4).

Figure 6:
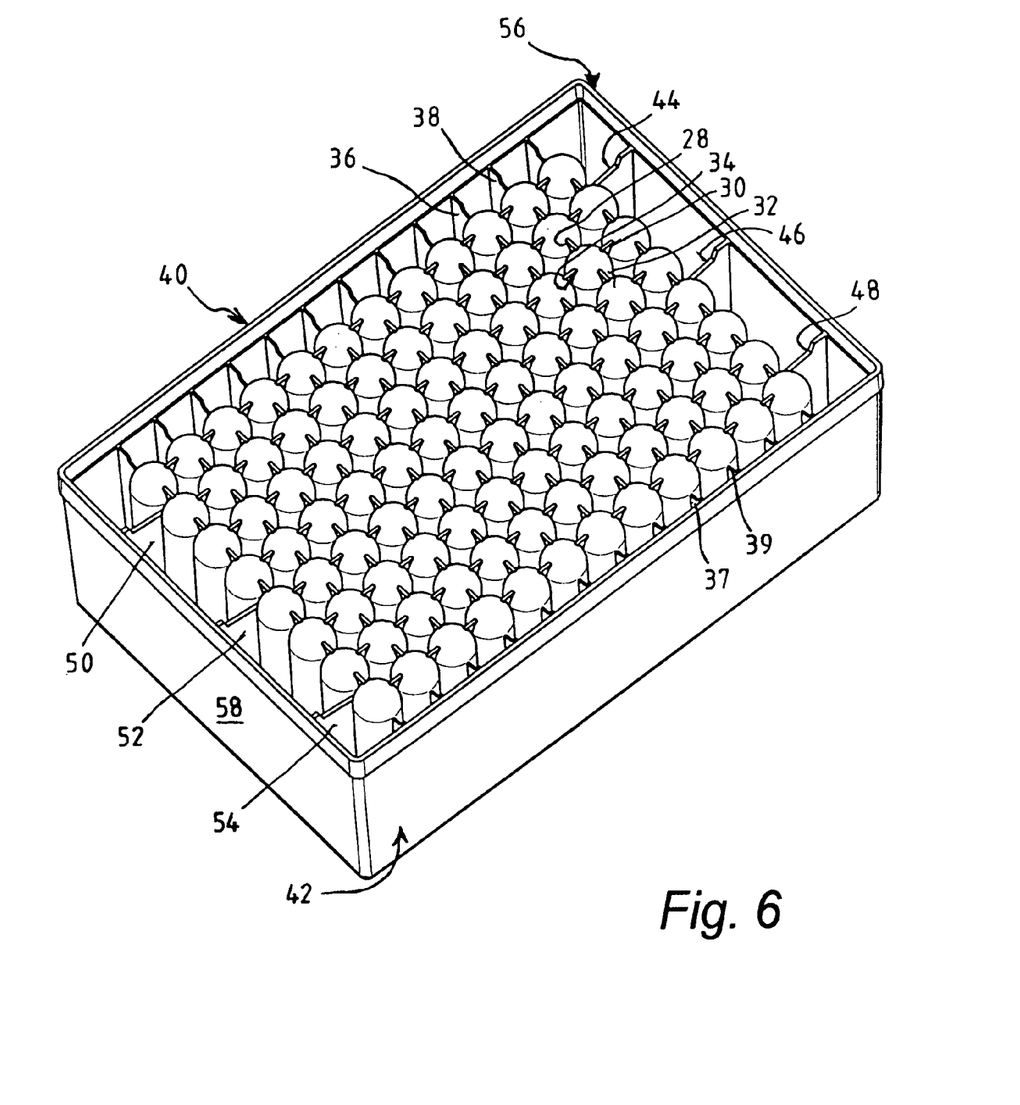
FIG. 6 is an underside perspective view of the microtitre well plate of the earlier Figures, showing the external underside shape of the wells and the bridging elements which extend therebetween.
Figure 7:
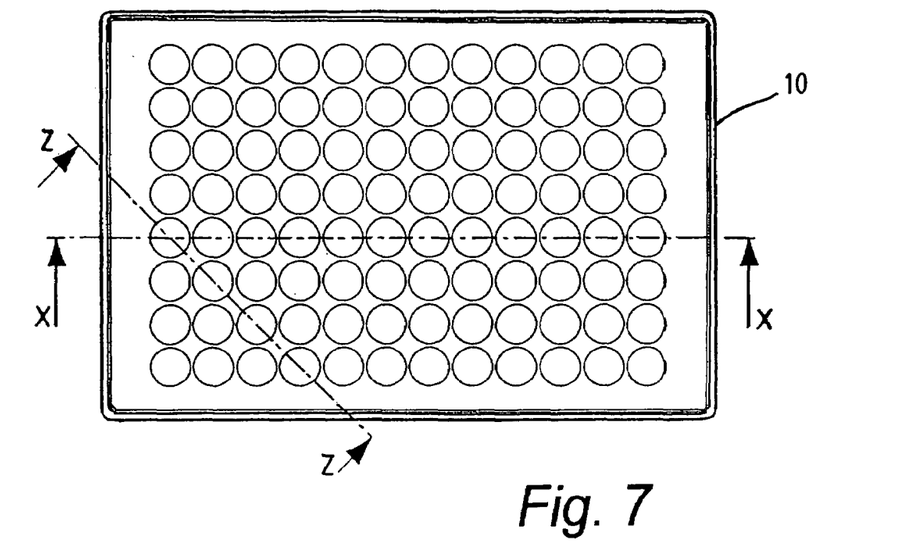
FIG. 7 is a plan view of the well housing from above.

As best seen in FIG. 6 the cylindrical well-wall exteriors merge one into the other where they touch, and ribs such as 28, 30, 32 and 34 (see FIG. 6) extend between the hemispherical ends as axial continuations of the junctions between the the adjoining wells. Between the outer line of wells on each perimeter of the well-array, additional ribs or webs such as 36, 38 (37, 39) extend between the cylindrical walls of the wells and the internal faces of the larger side walls 40, (42) respectively of the housing containing the well array. In a similar manner ribs or webs 44, 46, 48 (50, 52, 54) extend between junctions between adjoining wells in the shorter ends of the array and the shorter side walls 56, (58) respectively.

The ribs or webs 36-39 and 44-54 support the array of wells within the housing 10 while the interstitial ribs or webs such as 28-34 provide support between the adjacent wells.

Figure 5:
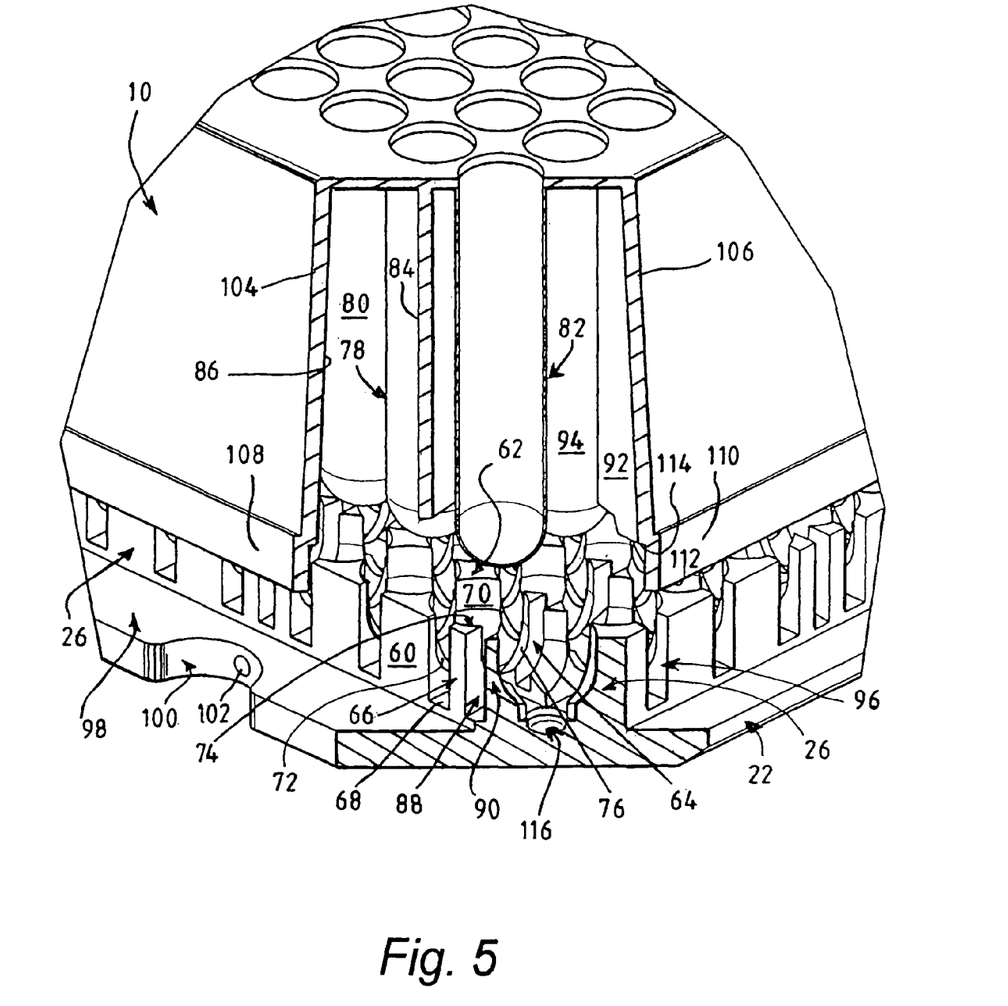
FIG. 5 is a similar perspective view to that of FIG. 3 but to a much enlarged scale showing the nearside corner of each component part cut-away to reveal the internal construction of the internal parts of the barrier plate which are adapted to be a snug fit around the wells.

The discontinuities in the platform 26 of the heat transfer plate form castellations with spaces therebetween which align with the ribs/webs such as 36-39 and 44-54, to accommodate them as the plate 22 is offered up to the underside of the well plate housing 10 and the platform region 26 is pushed into the open lower end thereof. This is best seen in FIG. 5 in which the nearside corner of the well plate housing 10, (shown to an enlarged scale) is cut-away (as is also the nearside corner of the thermal transfer plate and platform 22, 26). Four castellations 60, 62, 64, 66 upstanding from the base 68 of the platform 26 (itself carried by, and integrally formed with, the flat base of the plate 22), include four inwardly facing curved surfaces such as 70 in the case of castellation 62; 72 in the case of castellation 60; 74 in the case of castellation 66; and 76 in the case of castellation 64.

The upper regions of each of the four curved surfaces 70-76 are segments of a cylindrical surface corresponding to the cylindrical exterior of the well 78 which can thereby be lowered in between these surfaces. Lower down the four curved surfaces curve inwardly to define segments of a hemispherical surface corresponding to the hemispherical shape at the lower end of the well 78, so that when the well has been pushed into the cavity defined by these four castellations the lower curved end of the well is in contact with, and is a snug fit within, the four segments of the cylindrical and hemispherical surfaces defined by the four surfaces 70-76 on the four castellations 60-66.

The ribs or webs (not shown in FIG. 5) which extend between the walls of the well 78 and the adjoining wells, such as 80 and 82, and the rib or web 84 which extends from the junction between wells 78 and 82 and the outer wall 86 of the well housing 10, are accommodated in gaps between the castellations. In particular, web 84 will slide down the gap 88 between castellation 66 and adjoining castellation 90 (shown partly cut away). It will be appreciated that but for the gap 88, the two castellations 66 and 90 would form a single upstanding element similar in shape and cross section to castellation 60.

Where webs or ribs extend from a cylindrical surface of a well such as web 92 which extends from well 94, the web is accommodated in one of the regularly occurring gaps (such as 96 in this case) between the castellations forming the outer edge of the discontinuous platform 26.

It will be noted from FIG. 5 that the outer edge of the base 22 extends beyond the castellations to form a lip along each edge of the base, the nearer one of which is denoted by reference numeral 98 in FIG. 5. The lips extend by more than the thickness of the walls 86 of the well housing, and in the two shorter ends, the lips are cut away as shown at 100 in the case of lip 98 in FIG. 5, and the base is drilled at 102 to provide a location hole for an optional thermocouple temperature sensor.

By directing radiation towards the flat underside 24 of the plate 22 so as to heat the surface 24, heat will be transferred uniformly through the plate to the lower regions of the wells, via the upstanding castellations which embrace the lower ends of the wells.

As will be seen from the cut-away ends 104, 106 of the wall of the well housing 10, the lower edge of each section of the wall is stepped at 108, 110 respectively to form an internal ledge 112 for engaging the upper surfaces of the castellations over which the housing is fitted. The lowermost edge 112 of the housing 10 may thereby be supported clear of the upper surface of the base 22 extending outwardly to form the lip (such as 98 in FIG. 5). Alternatively, if the height of the ledge 114 is chosen appropriately, the edge 112 can just rest on the upper surface of base 22 when the ledge 114 engages the top of the castellations—or the engagement between 112 and base 22 may occur before 114 makes contact with the castellations.

Figure 8:
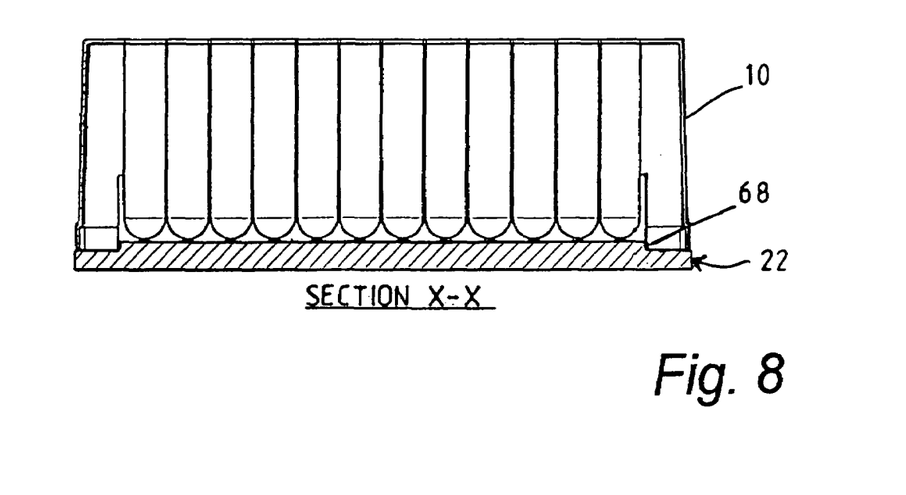
FIG. 8 is a cross section on the line XX of FIG. 7.

Referring once again to the cut away region of FIG. 5, it will be noted that a small conical depression 116 is formed in the upper surface of base 22 centrally of the four castellations adapted to receive the well 82. Although not shown a similar such depression is formed centrally of all the other groups of castellations which are to receive wells of the well plate. These depressions can also be seen in the cross sectional side elevation of FIG. 8.

The heat transfer plate 22 is most conveniently made from metal and a preferred metal is aluminium. Conveniently the microtitre plates are formed from moulded plastics material and at least the base if not also the walls of each well and the surrounding plate material is translucent if not transparent.

Figure 9:
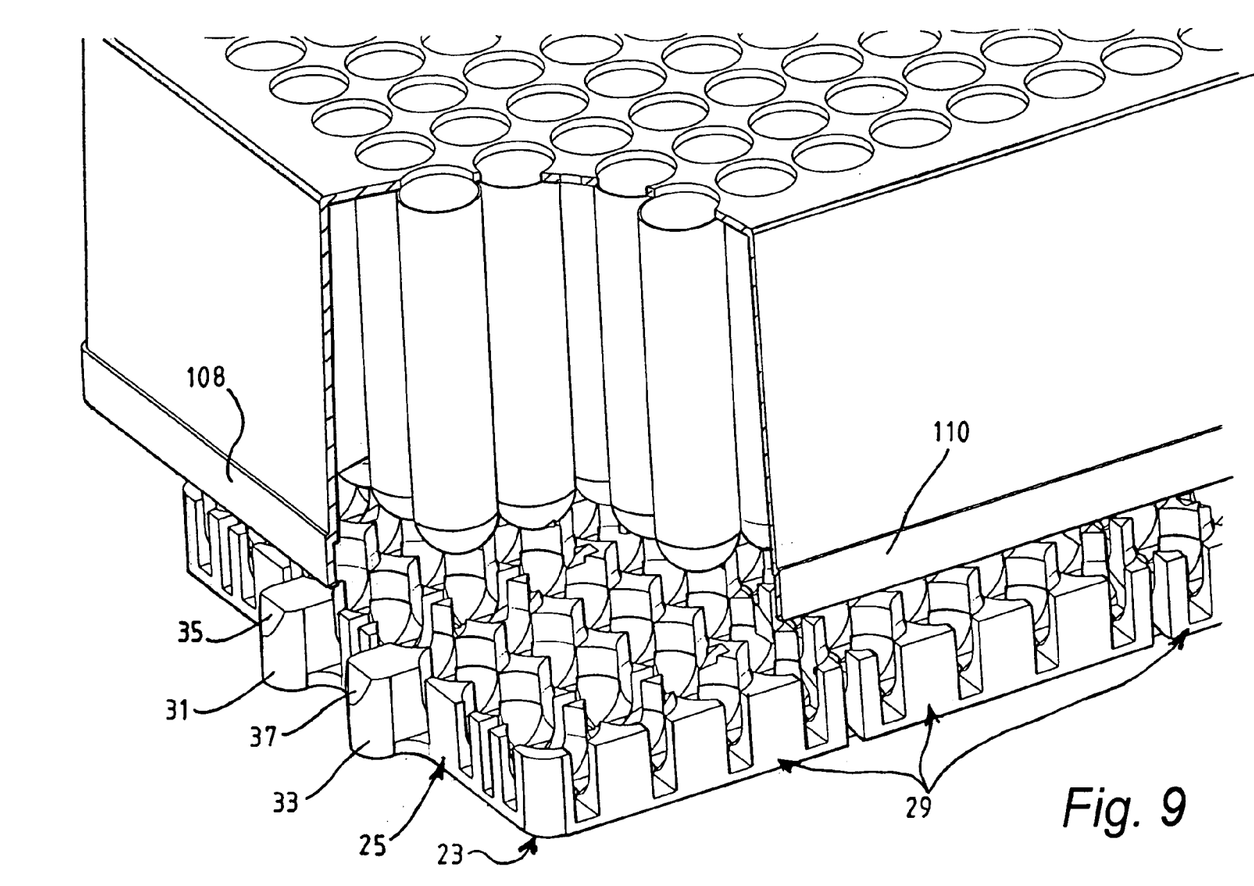
FIG. 9 is a cross-section similar to that of FIG. 8 of a microtitre well plate fitted with a modified barrier plate, which does not protrude beyond the envelope of the well plate.
Figure 10:
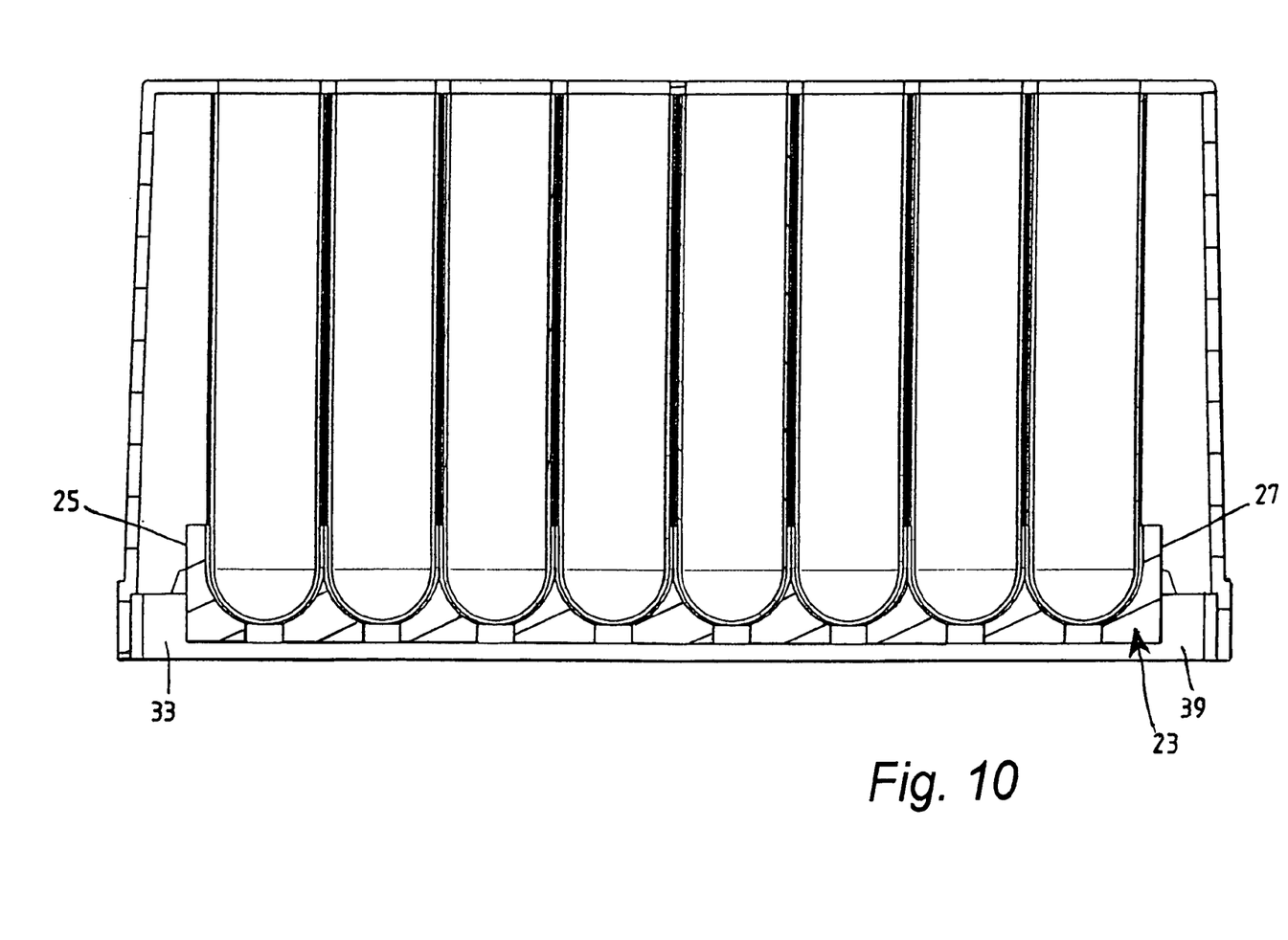
FIG. 10 is a perspective view similar to that of FIG. 5 showing how the modified barrier plate engages the inside of the well plate external wall.

As shown in FIGS. 9 and 10, the barrier plate 22 can be of reduced overall size as shown at 23 so that when fitted into the underside of a microtitre well plate housing 10, a gap will exist between at least the end faces 25 and 27 of the barrier plate 22, and the inside surface the plate and the side walls of the housing (such as 110 in FIG. 5). The near side edge is denoted generally by 29 in FIG. 9.

Clearly if so dimensioned the barrier plate 23 will not reliably remain attached to the lower ends of the wells and to this end protruding lugs as denoted by 31, 33 in FIG. 10 are provided along both opposite end faces 25, 27 of the barrier plate 23. Each lug is chamfered as at 35, 37 to assist in entry of the plate 23 into the underside of the well plate housing 10 and the inside wall surfaces may be indented to receive the lugs 31, 33 etc.

Only one of the pair of lugs at the opposite end is visible in FIG. 10, but is identified by reference numeral 39. Similar pairs of lugs (not shown) may be provided along the opposite side faces, such as 29, of the barrier plate 23. It will be seen that the plate 23, unlike plate 22, does not extend beyond the envelope of the well plate.

It has been proposed in GB 2,334,688 to provide a platform on a tray on which a microtitre well plate is located to engage a recessed underside of the mictrotitre plate, to improve the heat transfer between tray and plate. However this has not been found to satisfactorily increase heat transfer in practice due to the shape of the ends of the wells.

Control of pressure and speed of rotation of a centrifugal evaporator for difficult mixtures of solvents, is described in WO99/33538 published 8$^{th}$ Jul. 1999.

Details of the construction and operation of a centrifugal evaporator can be obtained from published GB Patent Specification 2,334,688, but the present invention represents an advance over the proposal contained in that earlier Patent Specification. In the present invention the convex undersides of the wells are in intimate contact with the faces of the upstanding castellations such as 60, 62, 64 and 66 which increases the area in contact and this greatly increases heat transfer as compared with a platform merely engaging the recessed underside of the well plate.

Figure 11:
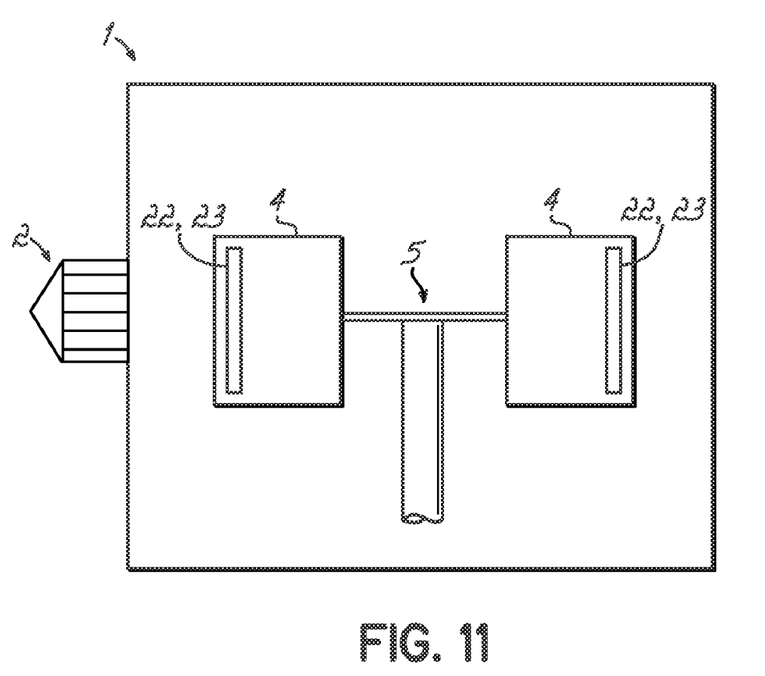
FIG. 11 is a diagrammatic view of an exemplary centrifugal evaporator in combination with the barrier plates of the present invention.

An exemplary centrifugal evaporator 1 is shown in FIG. 11 in combination with barrier plates as describes herein, by way of illustration. The barrier plates (22, 23) in FIG. 11 are carried by swinging sample holder support means 4 which are pivotally mounted on a rotatable table 5.

When the table 5 rotates, the support means 4 swing out to the position illustrated in which the sample wells are horizontal, under the influence of centrifugal force.

Heat is applied to the support means 4 by an infra-red radiation source 2, and radiant heat energy reaches the sample holder as illustrated.

The invention claimed is:

1. Heat transfer means for conveying infrared heat energy to a microtitre well plate which includes a plurality of wells, each well having an open end and a closed end comprising:
    a body which is substantially non-transmissive of radiation having wavelengths in the range 200 nm to 3000 nm and includes upstanding castellations which define a plurality of cavities configured to receive the closed ends of the wells, with each cavity being defined by a group of castellations, and the castellations in each group defining respective segments of a common hemispherical concave surface.

2. Heat transfer means as claimed in claim 1 wherein each of the cavities is defined by four castellations.

3. Heat transfer means as claimed in claim 1 including a plate of thermally conductive material which is of generally uniform thickness.

4. Heat transfer means as claimed in claim 3 including peripheral edges and protrusions along some or all of said edges for engaging a microtitre well plate.

5. A centrifugal evaporator in combination with heat transfer means, the combination comprising:

heat transfer means as claimed in claim 1, and a centrifugal evaporator, wherein the evaporator comprises an enclosure with a rotatable table therein, a swinging sample holder support means carried by the table configured to retain microtitre well plates therein, and infrared radiation heating means configured to heat the wells of each well plate via respective heat transfer means.

6. A method of protectively heating a microtitre well plate, the well plate including a plurality of wells, each well having an open end and a closed end, comprising the steps of:

placing the cavities of heat transfer means as claimed in claim 1 in contact with the closed ends of the wells of the well plate so that the cavities surround the closed ends, and heating the wells by directing infrared radiation towards the closed ends of the wells.

* * * * *